United States Patent [19]

Müller et al.

[11] Patent Number: 4,523,470

[45] Date of Patent: Jun. 18, 1985

[54] PROBE FOR THE NONDESTRUCTIVE TESTING OF CYLINDRICAL CAVITIES, ESPECIALLY OF STEAM GENERATOR TUBES

[75] Inventors: Thomas Müller; Günter Lehner, both of Erlangen; Georg Gugel, Kalchreuth, all of Fed. Rep. of Germany

[73] Assignee: Kraftwerk Union Aktiengesellschaft, Mülheim, Fed. Rep. of Germany

[21] Appl. No.: 462,047

[22] Filed: Jan. 28, 1983

[30] Foreign Application Priority Data

| Jan. 29, 1982 [DE] | Fed. Rep. of Germany | 3202931 |
| Jan. 29, 1982 [DE] | Fed. Rep. of Germany | 3202877 |
| Jan. 29, 1982 [DE] | Fed. Rep. of Germany | 8202241[U] |
| Jan. 29, 1982 [DE] | Fed. Rep. of Germany | 3202977 |
| Jan. 29, 1982 [DE] | Fed. Rep. of Germany | 8202128[U] |

[51] Int. Cl.³ ............................................. G01N 29/04
[52] U.S. Cl. .................................................... 73/623
[58] Field of Search ........................ 73/623, 638, 640

[56] References Cited

U.S. PATENT DOCUMENTS

| 2,825,044 | 2/1958 | Peterson | 73/623 |
| 3,636,778 | 1/1972 | Huffstetler | 73/623 |
| 4,037,465 | 7/1977 | Cook et al. | 73/623 |

Primary Examiner—Anthony V. Ciarlante
Attorney, Agent, or Firm—Herbert L. Lerner; Laurence A. Greenberg

[57] ABSTRACT

Probe for the nondestructive testing of cylindrical cavities, including a rotatable testing head, an outwardly cylindrical housing supporting the testing head, a motor disposed in the housing for driving the testing head, a shell body being surrounded by the housing and being in the form of a semi-cylindrical part with a relatively smaller diameter in vicinity of the motor, a tube sealing the shell body in vicinity of the motor, and means disposed on the shell body for securing the motor in a definite position.

10 Claims, 9 Drawing Figures

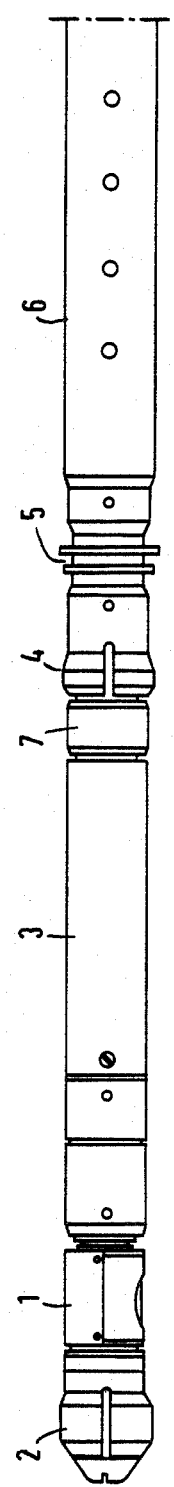
FIG 1
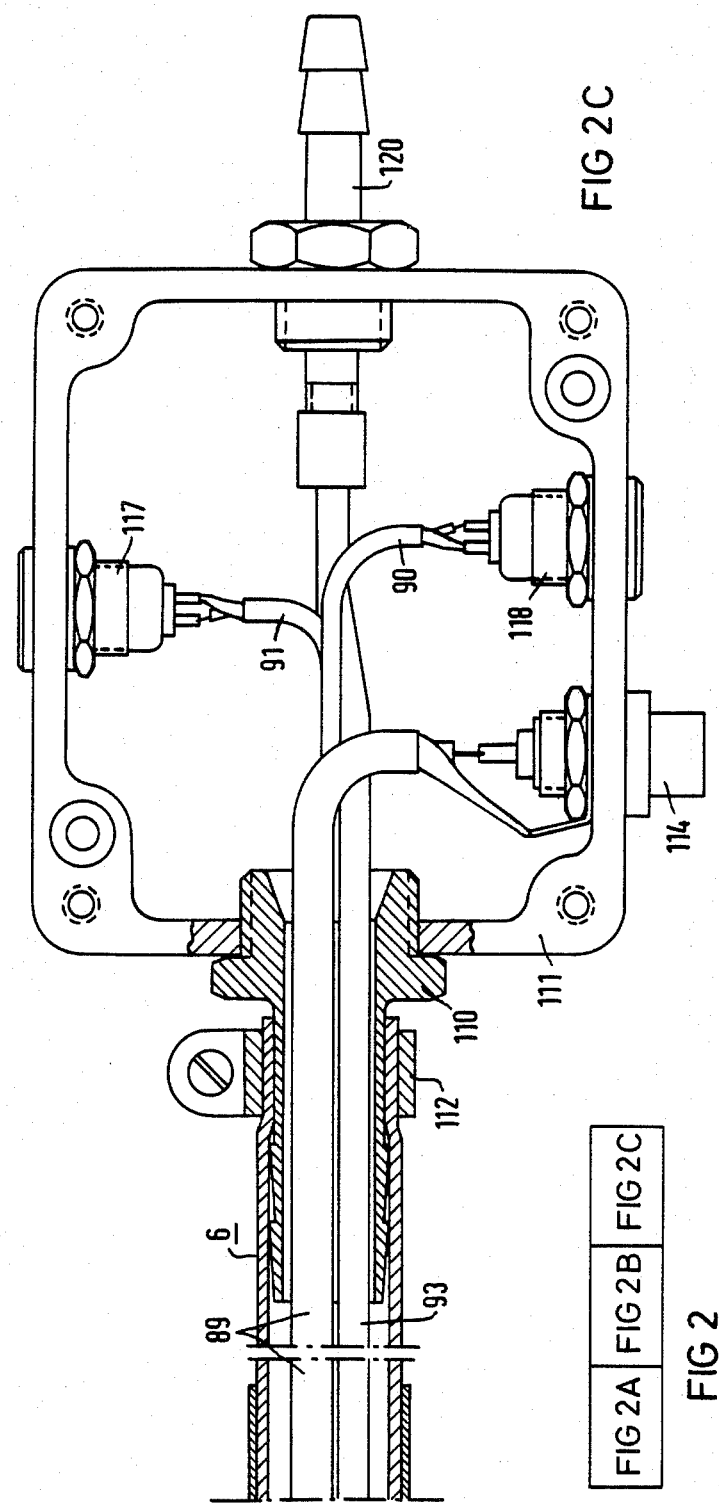
FIG 2C
| FIG 2A | FIG 2B | FIG 2C |
FIG 2

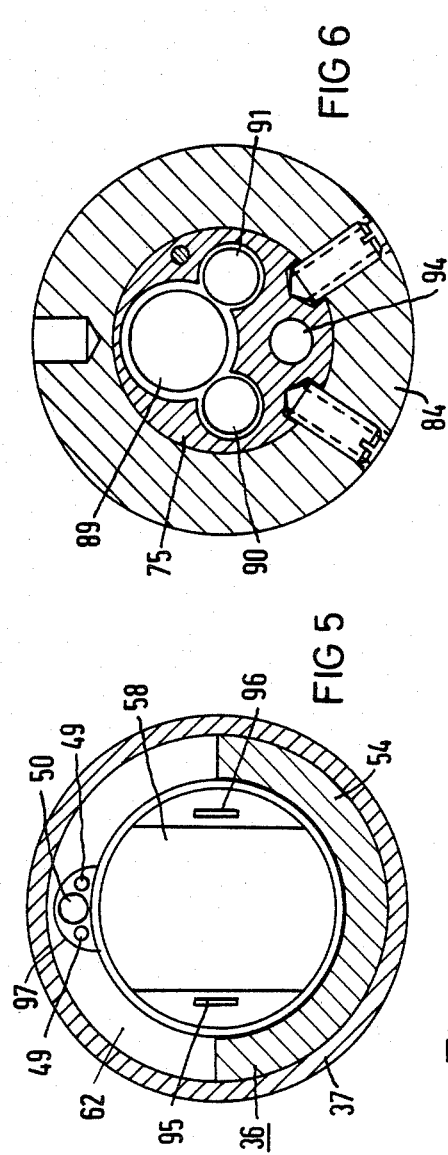
FIG 6
FIG 5
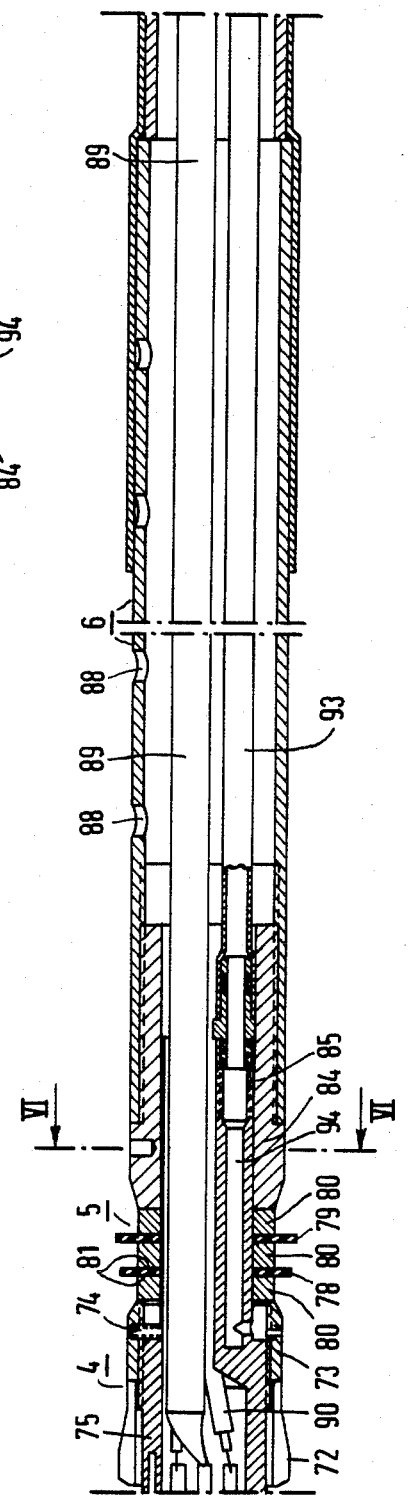
FIG 2B

PROBE FOR THE NONDESTRUCTIVE TESTING OF CYLINDRICAL CAVITIES, ESPECIALLY OF STEAM GENERATOR TUBES

The invention relates to a probe for the nondestructive testing of cylindrical cavities, especially steam generator tubes, with a rotating testing head which is supported in an outwardly cylindrical housing and is driven by a motor disposed therein. This construction is to be improved as far as production is concerned because it is important, due to the space conditions limited by the steam generator tubes, to make the motor as accessibly as possible while securing it well, so that it is easy to install and repair. It is accordingly an object of the invention to provide a probe for the nondestructive testing of cylindrical cavities, especially of steam generator tubes, which overcomes the hereinafore-mentioned disadvantages of the heretofore-known devices of this general type, and to improve the usefulness and reliability of the probe. The problem here is that the torque of the motor is very small because of the small motor dimensions, since the motor cannot be larger than the tubes to be tested, which as a rule have a diameter not exceeding 2 cm.

With the foregoing and other objects in view there is provided, in accordance with the invention, a probe for the nondestructive testing of cylindrical cavities, especially steam generator tubes, comprising a rotatable testing head, an outwardly cylindrical housing supporting the testing head, a motor disposed in the housing for driving the testing head, a shall body being surrounded by the housing and being in the form of a semicylindrical part with a relatively smaller diameter in vicinity of the motor, a tube sealing the shell body in vicinity of the motor, and means disposed on the shell body for securing the motor in a definite position. The shell body in this case provides for accurate fixation although the motor is substantially accessible because only the tube surrounding the shell body prevents access. On the other hand, the support is very space-saving because the shell body provides the strength necessary for the probe housing and the tube can therefore be thin-walled.

The fitting surface can advantageously comprise a cross piece extending transversely to the cylinder axis, into which a stub of the motor housing surrounding the motor shaft is inserted. The stub may have a thread for screwing into the shell body so that the fastening of the motor is ensured in a simple manner in addition to the fixation in space.

In accordance with another feature of the invention there is provided a shaft for the motor, a housing for the motor having a stub surrounding the motor shaft, and a cross piece extending transversely to the cylindrical housing being integral with the shell body, the securing means being in the form of a cylindrical bore hole formed in the cross piece, and the stub being inserted into the bore hole.

In accordance with a further feature of the invention, the stub has a thread formed thereon for screwing the stub into the shell body. It is possible thereby to construct the motor with a single fastening point; after the latter is released, the motor can be disassembled. At the same time, the testing head can be directly disengaged from the plug comnection toward the side facing away from the motor without the need to disassemble the motor separately. This allows fast replacement of defective testing heads.

In accordance with an additional feature of the invention, the motor has a shaft and the testing head has a drive shaft being supported in vicinity of the securing means, and including a plug connection coupling the motor shaft to the drive shaft.

In accordance with an added feature of the invention, the shell body has an end facing away from the testing head, and including a plug closing off the end of the shell body, and connecting lines for the motor and the testing head being carried by the plug. In this way, the strength of the shell body is utilized for forming a sealed space in which the motor is accommodated in a protected manner.

In accordance with yet another feature of the invention, the shell body has an end facing the testing head, and including slip rings, a drive shaft supporting the slip rings and coupling the slip rings to the testing head, and contact elements for the slip rings being disposed at the end of the shell body. Therefore, the electrical components which are particularly sensitive, are brought together in a protected manner in a common space. In addition, the handling is improved because the probe is easily replaceable due to the plug connection. Therefore, probes with signs of wear or trouble can be exchanged easily. At the same time, the watertight plug connection is used to seal the motor on one side, so that no additional elements are required and a lightweight construction is obtained which is also easy to move. The other seal is located on the "outside" of the space containing the motor and requires, as has been found, only small friction forces. Therefore, the small motor torque is practically completely available for moving the testing head and is not largely consumed by the forces required by the seal.

The slip rings can also serve as a simple but nevertheless very accurately operating device for determining the angular position. To this end, a rotor which is connected rigidly and directly to the testing head, is formed of two parts with different electric conductivity, of which one extends along the circumference of the rotor in the form of a narrow strip. Associated with the rotor are two brushes which conduct a current through the rotor that is different according to the conductivity of the strip. Thereby, an electrical signal is obtained in an angular position of the rotor given by the strip, so that the desired localization of faults is directly possible. If several strips with significantly different signals are used, such as strips with different brushes, the accuracy of the determination of the angular position can be increased further as desired.

In one embodiment of the invention, the strip consists of highly conductive material into which insulating material is embedded, and the brushes bear against the rotor, staggered in the longitudinal direction of the strip. They are connected through the strip if a given angular position of the rotor is reached.

Another embodiment of the invention, on the other hand, is constructed in such a way that the strip is formed of insulating material and that at least one brush has a contact area with a width smaller than the strip. The strip of insulating material then interrupts the electrical connection. The "smaller" contact area can also be obtained in this case by the provision that the insulating strip projects somewhat from the conductive rotor material and thereby lifts the brush off the conductive material.

In accordance with yet a further feature of the invention, the shell body has an end facing the testing head, and including a cap being screwed on the end of the shell body, and an antifriction bearing for the testing head being disposed in the cap.

In accordance with yet an additional feature of the invention there is provided, a V-ring seal being disposed on the outside of the cap and being braced against the testing head for sealing off the interior of the shell body. The V-ring seal is advantageously braced against the testing head, so that it is accommodated protected in a gap.

For testing steam generator tubes, an elastic ring seal can be provided at the cylindrical housing. This seal must meet stringent requirements because the tubes can have different inside diameters due to irregularities or encrustations or also because of the fabrication. At the same time, only small forces are permissible at the seal, so that the feed for the probe is not hindered. Therefore, the shell body has an end facing away from the testing head, and including metallic mounting bodies and an elastic ring seal formed of two flat rubber washers having different diameters and being clamped between the mounting bodies. Such a ring seal has been proven to be excellently in practical tests.

The difference of the diameters is advantageously as large as the thickness of the rubber washers. This, in turn, should be 1/15 to 1/30 of the diameters, which depends on the tubes to be tested. For instance, in tubes with a 20 mm diameters, this means that the thickness of the rubber washers is in the range of 1 mm. The difference between the diameters is then also in the same order of magnitude.

For securing the rubber washers, which is also important for the sealing action, the clamping pieces may advantageously be roughened on the surface facing the rubber washers, for instance by knurling.

In the testing head rotating about the axis, an ultrasonic vibrator acting radially to the axis may be disposed. While the ultrasonic vibrator is connected to the wall to be tested by a coupling medium, such as water, it would be advantageous if the vibrator of such ultrasonic probes could be fitted better to the cavities to be tested. To this end, the testing head has a radially extending hole formed therein, and including an ultrasonic vibrator being movably guided in the hole, and a clamping screw securing the vibrator. Thereby, it can be moved with little effort and thus adjusted or readjusted. For instance, large manufacturing tolerances of the tubes to be tested can be compensated thereby, so that a high sensitivity of the ultrasonic probe is always provided.

A particularly advantageous embodiment is that the clamping screw is a worm screw which is shorter than the length of the corresponding tapped hole, and that the threaded hole containing the worm screw is closed off by a further screw which is shorter than the difference of the lengths of the tapped hole and the worm screw. In this case, the tapped hole is additionally utilized as a structural element because, as the embodiment example will show in detail later on, it can carry a pointed plug forming the front of the probe.

For sealing the vibrator there is provided according to the invention, a shell-like metal plate closing off one side of the hole, and an O-ring sealing the vibrator on another side of the hole. It is thereby possible to keep the space which is desired for moving the vibrator free of liquid, so that the electric wires required to connect the vibrator need no special insulation.

Other features which are considered as characteristic for the invention are set forth in the appended claims.

Although the invention is illustrated and described herein as embodied in a probe for the nondestructive testing of cylindrical cavities, especially of steam generator tubes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing, in which:

FIG. 1 is a diagrammatic side elevational view of the probe of the invention as a whole;

FIGS. 2A, 2B and 2C are enlarged longitudinal-sectional views of the probe of FIG. 1; and FIGS. 3, 4, 5 and 6 are cross-sectional views of FIG. 2 taken along the lines III—III, IV—IV, V—V and VI—VI, respectively, therein, in the direction of the arrows.

Figure 3:
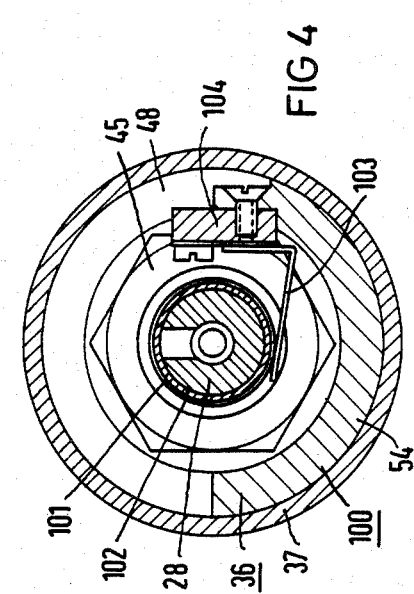

Referring now to the figures of the drawing in detail, and first particularly to FIG. 1 thereof, it is seen that the ultrasonic probe includes, as an essential part, a rotatable testing head 1 which is rotatably supported in a guide tip 2 and a cylindrical central part 3. The central part 3 is followed by a further guide part 4 with a sealing body 5, to which a thrust hose 6 is fastened. Between the guide part 4 and the central part 3, a plug connection 7 with a bayonet lock is provided.

Figure 2A:
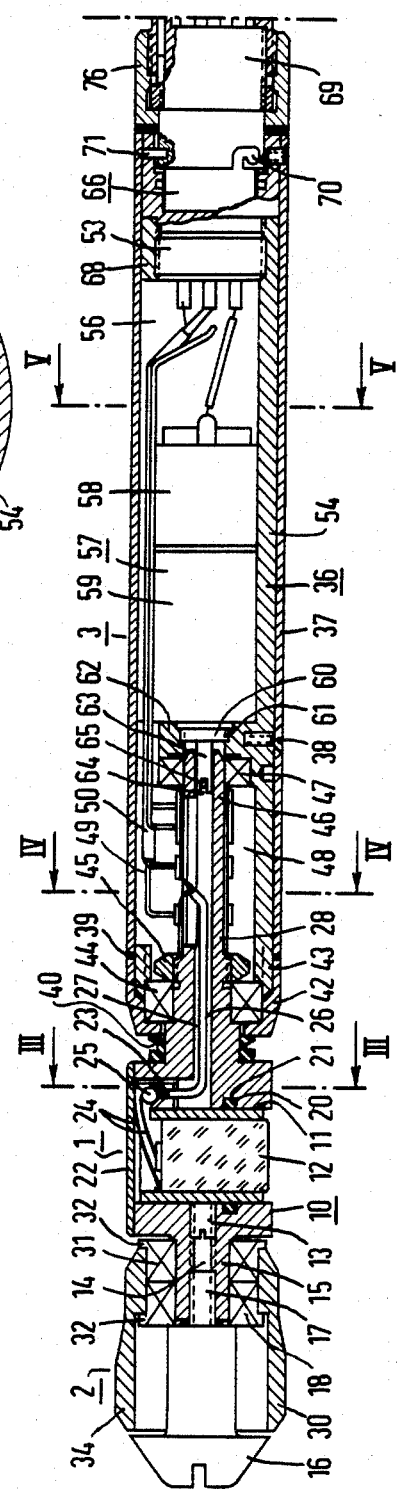

As seen in FIG. 2A, the testing head 1 includes a mounting body 10 which contains an ultrasonic vibrator 12 in a bore hole 11, that extends radially, i.e., transversely to the longitudinal axis of the probe. The ultrasonic vibrator is movably supported in the radial direction in the hole 11 and is clamped by means of a worm screw 13.

The worm screw 13 is disposed in a tapped hole 14 which extends through a shaft journal 15, on which the guide tip 2 is supported. As may be seen, the worm screw 13 is substantially shorter than the length of the tapped hole 14. A conically pointed end piece 16 with a post 17 is screwed into the free end of the hole 14. In this way, a ball bearing 18 is secured on the shaft journal 15. In addition, the tapped hole 14 is closed off by the end piece 16, so that the clamping of the vibrator 12 by the worm screw 13 is secured.

As may be seen, the bore hole 11 of the testing head 1 is provided with a slot 20 at one end in which an O-ring 21 provides a seal. The other end of the hole 11 is tightly closed off by a curved metal plate 22, which also covers a cavity 23 for receiving electric connecting lines 24 of the vibrator 12 and a trimming resistor 25 thereof. A cable 26 which is brought into the cavity 23, is led through a central hole 27 in a drive shaft 28, so that the testing head 1 is supported in the central part 3 and is connected to a drive designated as a whole with reference numeral 57. It may be seen in FIG. 3 that the plate 22 is adapted to the cylindrical shape of the mounting body 10, to which it is fastened by screws 105 shown in FIG. 3.

The guide tip 2 includes a slotted shell 30 which is held by the antifriction ball bearing 18 and by a second antifriction bearing 31 with flanges 32. The slotted shell 30 along with radially projecting fingers 34, forms laminations for guiding the probe at the tube wall to be tested.

The central part 3 has, as an essential component, a shell body 36 which is enclosed by a cylindrical tube 37 and is connected to the shell body 36 by a screw 38. The end of the shell body 36 facing the testing head 1 is closed off by a cap 42 which is screwed onto a thread 43 of the shell body 36, with a seal 39 being clamped between the cap 42 and the tube 37. A ball bearing 44 which is secured on the drive shaft by a ring nut 45 is mounted between the cap 42 and the drive shaft 28. A V-ring seal 40 is further clamped between the cap 42 and the mounting body 10 of the testing head 1.

An end 46 of the drive shaft 28 facing away from the testing head 1 is mounted in a second antifriction bearing 47 which is secured in the shell body 36. In the space 48 between the ring nut 45 and an antifriction bearing 47, various slip rings are disposed. With the slip rings, the electrical data of the vibrator 12 are transmitted through the cable 26 to stationary connecting leads which may be seen in the figure as cables 49 and 50 that lead to a connector 53 at the end of the shell body 36 facing away from the testing head 1.

The shell body 36 and a semi-cylindrical part 54 form a space 56 which is closed off at the top thereof by the tube 37. Disposed in the space 56 is a combination formed of an electric motor 58 and a reduction gear 59, as the drive for the testing head 1. The gear box structurally combined with the motor 58 is screwed by means of a threaded stub 60 into a central hole 61 with a cross piece 62 of the shell body 36, so that an accurately fitting fixation of the drive 57 is provided.

In vicinity of the cross plate 62, a transmission shaft 63 with a slot 64 is guided by a bolt 65 which extends through the hole 27 of the drive shaft 28. This structure forms a detachable plug coupling as a mechanical connection between the electric motor 58 and the testing head 1 to be rotated.

The connector or plug 53 is screwed into a hollow-cylindrical end 68 of the shell body 36 and is sealed, for instance, by filling the space 56 with synthetic casting resin. The plug 53 is part of a bayonet lock 66, having an angled-off slot 70 with which bolts 71 can engage. In this way, an easily detachable electrical and mechanical plug connection between the central part 3 and the guide part 4 is obtained.

Similar to the guide tip 2, the guide part 4 shown in FIG. 2B has an outwardly projecting enlargement 72 which is slotted in the lengthwise direction of the probe, so that lamella are produced. The enlargement belongs to a tube section 73 which is screwed onto an inner body 75 and is secured there by a screw 74. The inner body 75 encloses lines shown in FIG. 6, which will be described in detail later on and which lead to a plug connector 69 associated with the guide part 4, shown in FIG. 2A. The plug connector 69 is part of the bayonet lock 66 and is secured by a cap 76 in the form of a screw cap.

The seal designated as a whole with reference numeral 5 is disposed on the inner body 75. The seal 5 includes two flat rubber washers 78 and 79 which have a thickness of 0.8 mm and have two different outside diameters, namely 20 mm for the washer 78 and 21 mm for the washer 79. The two rubber washers 78, 79 are secured by means of three identical annular clamping rings 80 which have a surface which is roughened by knurling on end faces 81 facing the rubber washers 78, 79. The clamping rings 80 and the rubber washers 78, 79 are pressed together by pushing a tubular connecting body 84 on a shoulder 85 of the inner body 75.

The thrust hose 6 is mounted to the connecting body 84. The thrust hose is a plastic hose with an outside diameter of 18 mm and a wall thickness of 1.5 mm. The hose is formed, for instance, of polyethylene and has a perforation extending along a generatrix with circular holes 88 which have a diameter of 3 mm. The holes are disposed at a pitch or spacing T of 18 mm along the generatrix line of the cylindrical hose 6.

As shown in FIG. 6, the thrust hose 6 surrounds a coaxial cable 89 for transmitting the measurement data of the ultrasonic probe. A cable 90 serves for supplying voltage to the motor 58 which is preferably operated with d-c current. A further calbe 91 shown in FIG. 2C transmits pulses which are characteristic for the speed and the angular position of the testing head 1. In addition, a hose 93 which is in communication with a hole 94 formed in the inner body 75 is further accommodated in the thrust hose 6. Through the hose 93 liquid, preferably water, which serves for coupling the vibrator 12, can be conducted into the space which is closed off on one side by the washers 78 and 79.

FIG. 5 shows contacts 95 and 96 of the electric motor 58 which is surrounded by the semi-cylindrical part 54 of the shell body 36. FIG. 5 also shows the cables 49 and 50 running through a recess in the cross piece 62.

Figure 4:
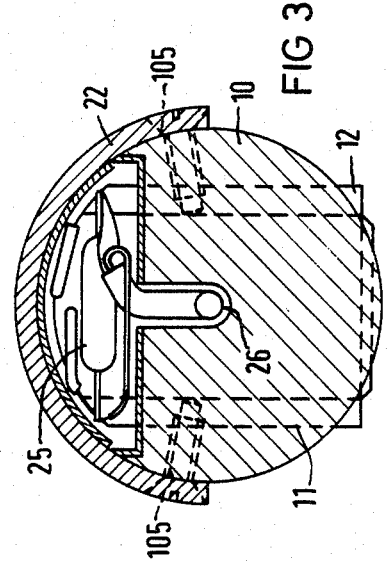

The cables 49 serve for the transmission of pulses which are generated by means of a multi-part slip ring 100. The slip ring is directly coupled to the testing head 1 by the drive shaft 28. In the embodiment according to FIG. 4, the slip ring 100 surrounds a metallic sleeve 101 which is electrically separated from the drive shaft 28 by an insulating sleeve 102. A resilient contact bracket 103 which is fastened to a stationary clamping point 104 slides on the metallic sleeve 101.

For generating pulses, the metallic sleeve 101 can be interrupted by insulating strips along a generatrix line. The insulating strips terminate the electrical contact between the slider 103 and the sleeve 101, depending on the angular position of the sleeve 101. The pulses are a measure of the speed of rotation of the testing head 1 and of its angular position. On the other hand, the measured ultrasonic values can be transmitted by the closed metallic sleeve 101, shown in FIG. 4, so that an extension of the cable 26 is provided over the slip rings by the cable 50. As shown in FIG. 2C, the end of the thrust hose 6 is clamped by a clamp 112 to a coupling piece 110 of a junction box 111. In the junction box 111, a feedthrough 114 for the coaxial cable 89 which carries the measurement values of the ultrasonic head 1, is provided. Two further feedthroughs 117 and 118 are provided for the connecting lines or further cables 90 and 91 which transmit the motor current and the pulse values characterizing the respective speed of rotation and angular position. A hose connection 120 is disposed at the box 111 for connecting the hose 93 for the coupling liquid.

There are claimed:

1. Probe for the nondestructive testing of cylindrical cavities, comprising a rotatable testing head, an outwardly cylindrical housing supporting said testing head, a motor disposed in said housing for driving said testing head, a shell body being surrounded by said housing and being in the form of a semi-cylindrical part with a relatively smaller diameter portion in vicinity of said motor, a tube sealing said shell body in vicinity of said motor, a shaft for said motor, a housing for said motor having a stub surrounding said motor shaft, and a cross piece extending transversely to said cylindrical housing being integral with said shell body, said cross piece having a cylindrical bore hole formed therein, and said stub being inserted into said bore hole for securing said motor in a definite position.

2. Probe according to claim 1, wherein said stub has a thread formed thereon for screwing said stub into said shell body.

3. Probe according to claim 1, wherein said motor has a shaft and said testing head has a drive shaft being supported in vicinity of said securing means, and including a plug connection coupling said motor shaft to said drive shaft.

4. Probe according to claim 1, wherein said shell body has an end facing away from said testing head, and including a plug closing off said end of said shell body, and connecting lines for said motor and said testing head being carried by said plug.

5. Probe according to claim 1, wherein said shell body has an end facing said testing head, and including slip rings, a drive shaft supporting said slip rings and coupling said slip rings to said testing head, and contact elements for said slip rings being disposed at said end of said shell body.

6. Probe according to claim 1, wherein said shell body has an end facing said testing head, and including a cap being screwed on said end of said shell body, and an antifriction bearing for said testing head being disposed in said cap.

7. Probe according to claim 6, including a V-ring seal being disposed on the outside of said cap and being braced against said testing head for sealing off the interior of said shell body.

8. Probe according to claim 1, wherein said shell body has an end facing away from said testing head, and including metallic mounting bodies and an elastic ring seal formed of two flat rubber washers having different diameters and being clamped between said mounting bodies.

9. Probe according to claim 1, wherein said testing head has a radially extending hole formed therein, and including an ultrasonic vibrator being movable guided in said hole, and a clamping screw securing said vibrator.

10. Probe according to claim 9, including a shell-like metal plate closing off one side of said hole, and an O-ring sealing said vibrator on another side of said hole.

* * * * *